United States Patent [19]

Epstein et al.

[11] Patent Number: 5,759,811
[45] Date of Patent: Jun. 2, 1998

[54] MUTANT HUMAN HEDGEHOG GENE

[75] Inventors: Ervin Epstein, Orinda; Zhilan Hu; Jeanette Bonifas, both of San Francisco, all of Calif.

[73] Assignee: The Regents of the University of California, Oakland, Calif.

[21] Appl. No.: 748,591

[22] Filed: Nov. 13, 1996

[51] Int. Cl.$^6$ .......................... C12P 21/06; C12N 15/00; C07K 1/00; C07H 21/02
[52] U.S. Cl. .................. 435/69.1; 435/320.1; 530/350; 536/23.1; 935/22
[58] Field of Search .................. 435/69.1, 320.1; 530/350; 536/23.1; 935/22

[56] References Cited

PUBLICATIONS

Oro et al. (1997) Basal cell carcinoma in mice overexpressing sonic hedgehog. Science 276: 817–821, May 2, 1997.
Fan et al. (1997) Induction to basal cell carcinoma features in transgenic human skin expressing sonic hedgehog. Nature Medicine 3 (7): 788–792, Jun. 1997.
Rudinger (1976) Characteristics of the amino as components of a peptide hormone sequence. In:Peptide Hormeones, Ed. J. A. Parsons, University park Press, Baltimore, MD, pp. 1–7, Jan. 1976.
Gailani et al. (1996) The role of the human homologue of Drosophila patched in sporadic basal cell carcinomas. Nature Genetics 14: 78–81, Sep. 14, 1998.
Roessler et al. (1996) Mutations in the human Sonic hedgehog gene cause holoprosencephaly. Nature Genetics 14: 357–360, Nov. 14, 1996.
Marigo et al. (1995) Cloning, expression and chromosomal location of SHH and IHH: Two human homologues of the Drosophila segment polarity gene hedgehog. Genomics 28: 44–51 Jul. 1, 1995.

Hahn et al. (1996) Mutations of the human homolog of Drosphila patched in the neviod basal cell carcinoma syndrome. Cell 85: 841–851, Jun. 14, 1996.
Hammerschmidt et al. (1997) The World according to hedgehog. Trends in Genetics 13(1): 14–21, Jan. 1, 1997.
Stone et al. (196) The tumor–suppressor gene patched encodes a candidate receptor for Sonic hedgehog. Nature 384: 129–134, Nov. 14, 1996.
Ogura et al. (1996) Evidence that Shh cooperates with a retinoic acid inducible co–factor to establish ZPA–like activity. Development 122: 537–542, Feb. 1996.

*Primary Examiner*—Robert A. Wax
*Assistant Examiner*—Einar Stole
*Attorney, Agent, or Firm*—Pamela J. Sherwood; Bozicevic & Reed LLP

[57] ABSTRACT

A mutation in the human sonic hedgehog gene is associated with tumorigenesis. A variety of human tumors, including basal cell carcinomas, breast carcinomas, medulloblastomas, etc., have a somatic mutation that results in an amino acid substitution at position 133 [*his133 SHH], or in a mutation at position 114. Such mutated genes and fragments thereof, encoded protein, and antibodies specific for the mutated protein are useful in characterizing the phenotype of associated tumors. The mutant protein is useful in drug screening for compositions that antagonize or otherwise modulate HH activity or expression. The encoded protein is also used as a therapeutic, to modulate cell proliferation and differentiation, and treatment of pathological conditions associated with decreased hedgehog signaling.

17 Claims, No Drawings

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asn Ala Leu Ala Ile Ala Val Met Asn Met Trp Pro Gly Val Arg Leu
 1               5                  10                  15
Arg Val Thr Glu Gly Trp Asp Glu Asp Gly His His Ala Gln
            20                  25                  30
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asn Ala Leu Ala Ile Ser Val Met Asn Gln Trp Pro Gly Val Lys Leu
 1               5                  10                  15
Arg Val Thr Glu Gly Trp Asp Glu Asp Gly His His Ser Glu
            20                  25                  30
```

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asn  Ser  Leu  Ala  Ile  Ser  Val  Met  Asn  Gln  Trp  Pro  Gly  Val  Lys  Leu
1              5                        10                       15

Arg  Val  Thr  Glu  Gly  Trp  Asp  Glu  Asp  Gly  His  His  Ser  Glu
               20                       25                       30
```

( 2 ) INFORMATION FOR SEQ ID NO:4:

( i ) SEQUENCE CHARACTERISTICS:
( A ) LENGTH: 462 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

```
Met  Leu  Leu  Leu  Ala  Arg  Cys  Leu  Leu  Val  Leu  Val  Ser  Ser  Leu
1              5                        10                       15

Leu  Val  Cys  Ser  Gly  Leu  Ala  Cys  Gly  Pro  Gly  Arg  Gly  Phe  Gly  Lys
               20                       25                       30

Arg  Arg  His  Pro  Lys  Lys  Leu  Thr  Pro  Leu  Ala  Tyr  Lys  Gln  Phe  Ile
               35                       40                       45

Pro  Asn  Val  Ala  Glu  Lys  Thr  Leu  Gly  Ala  Ser  Gly  Arg  Tyr  Glu  Gly
          50                       55                       60

Lys  Ile  Ser  Arg  Asn  Ser  Glu  Arg  Phe  Lys  Glu  Leu  Thr  Pro  Asn  Tyr
65                       70                       75                       80

Asn  Pro  Asp  Ile  Ile  Phe  Lys  Asp  Glu  Glu  Asn  Thr  Gly  Ala  Asp  Arg
                    85                       90                       95

Leu  Met  Thr  Gln  Arg  Cys  Lys  Asp  Lys  Leu  Asn  Ala  Leu  Ala  Ile  Ser
               100                      105                      110

Val  Met  Asn  Gln  Trp  Pro  Gly  Val  Lys  Leu  Arg  Val  Thr  Glu  Gly  Trp
               115                      120                      125

Asp  Glu  Asp  Gly  His  His  Ser  Glu  Glu  Ser  Leu  His  Tyr  Glu  Gly  Arg
          130                      135                      140

Ala  Val  Asp  Ile  Thr  Thr  Ser  Asp  Arg  Asp  Arg  Ser  Lys  Tyr  Gly  Met
145                      150                      155                      160

Leu  Ala  Arg  Leu  Ala  Val  Glu  Ala  Gly  Phe  Asp  Trp  Val  Tyr  Tyr  Glu
               165                      170                      175

Ser  Lys  Ala  His  Ile  His  Cys  Ser  Val  Lys  Ala  Glu  Asn  Ser  Val  Ala
               180                      185                      190

Ala  Lys  Ser  Gly  Gly  Cys  Phe  Pro  Gly  Ser  Ala  Thr  Val  His  Leu  Glu
               195                      200                      205

Gln  Gly  Gly  Thr  Lys  Leu  Val  Lys  Asp  Leu  Ser  Pro  Gly  Asp  Arg  Val
          210                      215                      220

Leu  Ala  Ala  Asp  Asp  Gln  Gly  Arg  Leu  Leu  Tyr  Ser  Asp  Phe  Leu  Thr
225                      230                      235                      240

Phe  Leu  Asp  Arg  Asp  Asp  Gly  Ala  Lys  Lys  Val  Phe  Tyr  Val  Ile  Glu
               245                      250                      255

Thr  Arg  Glu  Pro  Arg  Glu  Arg  Leu  Leu  Leu  Thr  Ala  Ala  His  Leu  Leu
               260                      265                      270

Phe  Val  Ala  Pro  His  Asn  Asp  Ser  Ala  Thr  Gly  Glu  Pro  Glu  Ala  Ser
               275                      280                      285

Ser  Gly  Ser  Gly  Pro  Pro  Ser  Gly  Gly  Ala  Leu  Gly  Pro  Arg  Ala  Leu
          290                      295                      300

Phe  Ala  Ser  Arg  Val  Arg  Pro  Gly  Gln  Arg  Val  Tyr  Val  Val  Ala  Glu
```

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |

Arg Asp Gly Asp Arg Arg Leu Leu Pro Ala Ala Val His Ser Val Thr
            325             330             335

Leu Ser Glu Glu Ala Ala Gly Ala Tyr Ala Pro Leu Thr Ala Gln Gly
        340             345             350

Thr Ile Leu Ile Asn Arg Val Leu Ala Ser Cys Tyr Ala Val Ile Glu
        355             360             365

Glu His Ser Trp Ala His Arg Ala Phe Ala Pro Phe Arg Leu Ala His
    370             375             380

Ala Leu Leu Ala Ala Leu Ala Pro Ala Arg Thr Asp Arg Gly Gly Asp
385             390             395             400

Ser Gly Gly Gly Asp Arg Gly Gly Gly Gly Arg Val Ala Leu Thr
            405             410             415

Ala Pro Gly Ala Ala Asp Ala Pro Gly Ala Gly Ala Thr Ala Gly Ile
            420             425             430

His Trp Tyr Ser Gln Leu Leu Tyr Gln Ile Gly Thr Trp Leu Leu Asp
        435             440             445

Ser Glu Ala Leu His Pro Leu Gly Met Ala Val Lys Ser Ser
    450             455             460

(2) INFORMATION FOR SEQ ID NO:5:

(i) SEQUENCE CHARACTERISTICS:
        (A) LENGTH: 1576 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
GCGAGGCAGC CAGCGAGGGA GAGAGCGAGC GGGCGAGCCG GAGCGAGGAA GGGAAAGCGC      60
AAGAGAGAGC GCACACGCAC ACACCCGCCG CGCGCACTCG CGCCCGGACC CGCACGGGGA     120
CAGCTCGGAA GTCATCAGTT CCATGGGCGA GATGCTGCTG CTGGCGAGAT GTCTGCTGCT     180
AGTCCTCGTC TCCTCGCTGC TGGTATGCTC GGGACTGGCG TGCGGACCGG GCAGGGGGTT     240
CGGGAAGAGG AGGCACCCCA AAAAGCTGAC CCCTTTAGCC TACAAGCAGT TTATCCCCAA     300
TGTGGCCGAG AAGACCCTAG GCGCCAGCGG AAGGTATGAA GGGAAGATCT CCAGAAACTC     360
CGAGCGATTT AAGGAACTCA CCCCCAATTA CAACCCCGAC ATCATATTTA AGGATGAAGA     420
AAACACCGGA GCGGACAGGC TGATGACTCA GAGGTGTAAG GACAAGTTGA ACGCTTTGGC     480
CATCTCGGTG ATGAACCAGT GGCCAGGAGT GAAACTGCGG GTGACCGAGG GCTGGGACGA     540
AGATGGCTAC CACTCAGAGG AGTCTCTGCA CTACGAGGGC CGCGCAGTGG ACATCACCAC     600
GTCTGACCGC GACCGCAGCA AGTACGGCAT GCTGGCCCGC TGGCGGTGG AGGCCGGCTT     660
CGACTGGGTG TACTACGAGT CCAAGGCACA TATCCACTGC TCGGTGAAAG CAGAGAACTC     720
GGTGGCGGCC AAATCGGGAG GCTGCTTCCC GGGCTCGGCC ACGGTGCACC TGGAGCAGGG     780
CGGCACCAAG CTGGTGAAGG ACCTGAGCCC CGGGGACCGC GTGCTGGCGG CGGACGACCA     840
GGGCCGGCTG CTCTACAGCG ACTTCCTCAC TTTCCTGGAC CGCGACGACG GCGCCAAGAA     900
GGTCTTCTAC GTGATCGAGA CGCGGGAGCC GCGCGAGCGC CTGCTGCTCA CCGCCGCGCA     960
CCTGCTCTTT GTGGCGCCGC ACAACGACTC GGCCACCGGG GAGCCCGAGG CGTCCTCGGG    1020
CTCGGGGCCG CCTTCCGGGG GCGCACTGGG GCCTCGGGCG CTGTTCGCCA GCCGCGTGCG    1080
CCCGGGCCAG CGCGTGTACG TGGTGGCCGA GCGTGACGGG GACCGCCGGC TCCTGCCCGC    1140
```

```
CGCTGTGCAC AGCGTGACCC TAAGCGAGGA GGCCGCGGGC GCCTACGCGC CGCTCACGGC    1200

CCAGGGCACC ATTCTCATCA ACCGGGTGCT GGCCTCGTGC TACGCGGTCA TCGAGGAGCA    1260

CAGCTGGGCG CACCGGGCCT TCGCGCCCTT CCGCCTGGCG CACGCGCTCC TGGCTGCACT    1320

GGCGCCCGCG CGCACGGACC GCGGCGGGGA CAGCGGCGGC GGGGACCGCG GGGGCGGCGG    1380

CGGCAGAGTA GCCCTAACCG CTCCAGGTGC TGCCGACGCT CCGGGTGCGG GGGCCACCGC    1440

GGGCATCCAC TGGTACTCGC AGCTGCTCTA CCAAATAGGC ACCTGGCTCC TGGACAGCGA    1500

GGCCCTGCAC CCGCTGGGCA TGGCGGTCAA GTCCAGCTGA AGCCGGGGGG CCGGGGAGG     1560

GGCGCGGGAG GGGGCC                                                    1576
```

( 2 ) INFORMATION FOR SEQ ID NO:6:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Arg Val Asn Ala Leu Ala Ile Ala Val Met Asn Met Trp Pro Gly Val
 1               5                  10                  15

Arg Leu Arg Val Thr Glu Gly Trp Asp Glu Asp
            20                  25
```

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Lys Leu Asn Ala Leu Ala Ile Ser Val Met Asn Gln Trp Pro Gly Val
 1               5                  10                  15

Lys Leu Arg Val Thr Glu Gly Trp Asp Glu Asp
            20                  25
```

( 2 ) INFORMATION FOR SEQ ID NO:8:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Arg Leu Asn Ser Leu Ala Ile Ser Val Met Asn Gln Trp Pro Gly Val
 1               5                  10                  15

Lys Leu Arg Val Thr Glu Gly Trp Asp Glu Asp
            20                  25
```

( 2 ) INFORMATION FOR SEQ ID NO:9:

( i ) SEQUENCE CHARACTERISTICS:
        ( A ) LENGTH: 462 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:9:

| Met | Leu | Leu | Leu | Ala | Arg | Cys | Leu | Leu | Val | Leu | Val | Ser | Ser | Leu |
|---|---|---|---|---|---|---|---|---|---|---|---|---|---|---|
| 1 | | | | 5 | | | | | 10 | | | | | 15 |
| Leu | Val | Cys | Ser | Gly | Leu | Ala | Cys | Gly | Pro | Gly | Arg | Gly | Phe | Gly | Lys |

Met Leu Leu Leu Ala Arg Cys Leu Leu Val Leu Val Ser Ser Leu
1                  5                        10                      15
Leu Val Cys Ser Gly Leu Ala Cys Gly Pro Gly Arg Gly Phe Gly Lys
                20                      25                      30
Arg Arg His Pro Lys Lys Leu Thr Pro Leu Ala Tyr Lys Gln Phe Ile
         35                      40                      45
Pro Asn Val Ala Glu Lys Thr Leu Gly Ala Ser Gly Arg Tyr Glu Gly
     50                      55                      60
Lys Ile Ser Arg Asn Ser Glu Arg Phe Lys Glu Leu Thr Pro Asn Tyr
65                      70                      75                      80
Asn Pro Asp Ile Ile Phe Lys Asp Glu Glu Asn Thr Gly Ala Asp Arg
                     85                      90                      95
Leu Met Thr Gln Arg Cys Lys Asp Lys Leu Asn Ala Leu Ala Ile Ser
             100                     105                     110
Val Met Asn Gln Trp Pro Gly Val Lys Leu Arg Val Thr Glu Gly Trp
         115                     120                     125
Asp Glu Asp Gly His His Ser Glu Glu Ser Leu His Tyr Glu Gly Arg
     130                     135                     140
Ala Val Asp Ile Thr Thr Ser Asp Arg Asp Arg Ser Lys Tyr Gly Met
145                     150                     155                     160
Leu Ala Arg Leu Ala Val Glu Ala Gly Phe Asp Trp Val Tyr Tyr Glu
                 165                     170                     175
Ser Lys Ala His Ile His Cys Ser Val Lys Ala Glu Asn Ser Val Ala
             180                     185                     190
Ala Lys Ser Gly Gly Cys Phe Pro Gly Ser Ala Thr Val His Leu Glu
         195                     200                     205
Gln Gly Gly Thr Lys Leu Val Lys Asp Leu Ser Pro Gly Asp Arg Val
     210                     215                     220
Leu Ala Ala Asp Asp Gln Gly Arg Leu Leu Tyr Ser Asp Phe Leu Thr
225                     230                     235                     240
Phe Leu Asp Arg Asp Asp Gly Ala Lys Lys Val Phe Tyr Val Ile Glu
                 245                     250                     255
Thr Arg Glu Pro Arg Glu Arg Leu Leu Leu Thr Ala Ala His Leu Leu
             260                     265                     270
Phe Val Ala Pro His Asn Asp Ser Ala Thr Gly Glu Pro Glu Ala Ser
         275                     280                     285
Ser Gly Ser Gly Pro Pro Ser Gly Gly Ala Leu Gly Pro Arg Ala Leu
     290                     295                     300
Phe Ala Ser Arg Val Arg Pro Gly Gln Arg Val Tyr Val Val Ala Glu
305                     310                     315                     320
Arg Asp Gly Asp Arg Arg Leu Leu Pro Ala Ala Val His Ser Val Thr
                 325                     330                     335
Leu Ser Glu Glu Ala Ala Gly Ala Tyr Ala Pro Leu Thr Ala Gln Gly
             340                     345                     350
Thr Ile Leu Ile Asn Arg Val Leu Ala Ser Cys Tyr Ala Val Ile Glu
         355                     360                     365
Glu His Ser Trp Ala His Arg Ala Phe Ala Pro Phe Arg Leu Ala His
     370                     375                     380
Ala Leu Leu Ala Ala Leu Ala Pro Ala Arg Thr Asp Arg Gly Gly Asp
385                     390                     395                     400

| | | | | | | | | | | | | | | |
|---|---|---|---|---|---|---|---|---|---|---|---|---|---|---|
|Ser|Gly|Gly|Gly|Asp|Arg|Gly|Gly|Gly|Gly|Arg|Val|Ala|Leu|Thr|
| | | | |405| | | |410| | | | |415| |
|Ala|Pro|Gly|Ala|Ala|Asp|Ala|Pro|Gly|Ala|Gly|Ala|Thr|Ala|Gly|Ile|
| | | |420| | | |425| | | | |430| | |
|His|Trp|Tyr|Ser|Gln|Leu|Leu|Tyr|Gln|Ile|Gly|Thr|Trp|Leu|Leu|Asp|
| | |435| | | | |440| | | | |445| | |
|Ser|Glu|Ala|Leu|His|Pro|Leu|Gly|Met|Ala|Val|Lys|Ser|Ser|
| |450| | | |455| | | | |460| | | |

( 2 ) INFORMATION FOR SEQ ID NO:10:

( i ) SEQUENCE CHARACTERISTICS:
( A ) LENGTH: 1576 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
|GCGAGGCAGC|CAGCGAGGGA|GAGAGCGAGC|GGGCGAGCCG|GAGCGAGGAA|GGGAAAGCGC|60|
|AAGAGAGAGC|GCACACGCAC|ACACCCGCCG|CGCGCACTCG|CGCCCGGACC|CGCACGGGA|120|
|CAGCTCGGAA|GTCATCAGTT|CCATGGGCGA|GATGCTGCTG|CTGGCGAGAT|GTCTGCTGCT|180|
|AGTCCTCGTC|TCCTCGCTGC|TGGTATGCTC|GGGACTGGCG|TGCGGACCGG|GCAGGGGGTT|240|
|CGGGAAGAGG|AGGCACCCCA|AAAAGCTGAC|CCCTTTAGCC|TACAAGCAGT|TTATCCCCAA|300|
|TGTGGCCGAG|AAGACCCTAG|GCGCCAGCGG|AAGGTATGAA|GGGAAGATCT|CCAGAAACTC|360|
|CGAGCGATTT|AAGGAACTCA|CCCCCAATTA|CAACCCCGAC|ATCATATTTA|AGGATGAAGA|420|
|AAACACCGGA|GCGGACAGGC|TGATGACTCA|GAGGTGTAAG|ACAAGTTGA|ACGCTTTGGC|480|
|CATCTCGGTG|ATAAACCAGT|GGCCAGGAGT|GAAACTGCGG|GTGACCGAGG|GCTGGGACGA|540|
|AGATGGCCAC|CACTCAGAGG|AGTCTCTGCA|CTACGAGGGC|CGCGCAGTGG|ACATCACCAC|600|
|GTCTGACCGC|GACCGCAGCA|AGTACGGCAT|GCTGGCCCGC|CTGGCGGTGG|AGGCCGGCTT|660|
|CGACTGGGTG|TACTACGAGT|CCAAGGCACA|TATCCACTGC|TCGGTGAAAG|CAGAGAACTC|720|
|GGTGGCGGCC|AAATCGGGAG|GCTGCTTCCC|GGGCTCGGCC|ACGGTGCACC|TGGAGCAGGG|780|
|CGGCACCAAG|CTGGTGAAGG|ACCTGAGCCC|CGGGGACCGC|GTGCTGGCGG|CGGACGACCA|840|
|GGGCCGGCTG|CTCTACAGCG|ACTTCCTCAC|TTTCCTGGAC|CGCGACGACG|GCGCCAAGAA|900|
|GGTCTTCTAC|GTGATCGAGA|CGCGGGAGCC|GCGCGAGCGC|CTGCTGCTCA|CCGCCGCGCA|960|
|CCTGCTCTTT|GTGGCGCCGC|ACAACGACTC|GGCCACCGGG|GAGCCCGAGG|CGTCCTCGGG|1020|
|CTCGGGGCCG|CCTTCCGGGG|GCGCACTGGG|GCCTCGGGCG|CTGTTCGCCA|GCCGCGTGCG|1080|
|CCCGGGCCAG|CGCGTGTACG|TGGTGGCCGA|GCGTGACGGG|GACCGCCGGC|TCCTGCCCGC|1140|
|CGCTGTGCAC|AGCGTGACCC|TAAGCGAGGA|GGCCGCGGGC|GCCTACGCGC|CGCTCACGGC|1200|
|CCAGGGCACC|ATTCTCATCA|ACCGGGTGCT|GGCCTCGTGC|TACGCGGTCA|TCGAGGAGCA|1260|
|CAGCTGGGCG|CACCGGGCCT|TCGCGCCCTT|CCGCCTGGCG|CACGCGCTCC|TGGCTGCACT|1320|
|GGCGCCCGCG|CGCACGGACC|GCGGCGGGGA|CAGCGGCGGC|GGGGACCGCG|GGGCGGCGG|1380|
|CGGCAGAGTA|GCCCTAACCG|CTCCAGGTGC|TGCCGACGCT|CCGGGTGCGG|GGCCACCGC|1440|
|GGGCATCCAC|TGGTACTCGC|AGCTGCTCTA|CCAAATAGGC|ACCTGGCTCC|TGGACAGCGA|1500|
|GGCCCTGCAC|CCGCTGGGCA|TGGCGGTCAA|GTCCAGCTGA|AGCCGGGGGG|CCGGGGGAGG|1560|
|GGCGCGGGAG|GGGGCC| | | | |1576|

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ACCGAGGGCT GGGACGAAGA TGGC        24

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GCGAGCCAGC ATGCCGTACT TGCTG        25

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CCGCCGCGCG CACTCG        16

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

AAGGAGCGGG TGAAATCACC        20

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TAACGTGTCC GTCGGTGGG        19

( 2 ) INFORMATION FOR SEQ ID NO:16:

( i ) SEQUENCE CHARACTERISTICS:
        ( A ) LENGTH: 19 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

TGCTTTCACC GAGCAGTGG 19

(2) INFORMATION FOR SEQ ID NO:17:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

CCTCCTCCCC GAGACGC 17

(2) INFORMATION FOR SEQ ID NO:18:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

GGCCCCCTCC CGCGCC 16

(2) INFORMATION FOR SEQ ID NO:19:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

CCGCCGCGCG CACTCG 16

(2) INFORMATION FOR SEQ ID NO:20:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:20:

GGCCCCCTCC CGCGCC 16

(2) INFORMATION FOR SEQ ID NO:21:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:21:

GTCCTTCACC AGCTTGGTG  19

( 2 ) INFORMATION FOR SEQ ID NO:22:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:22:

TGCCCACCGG GCAGGGGG  18

( 2 ) INFORMATION FOR SEQ ID NO:23:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:23:

TCAGCCTCCC ATTTGGCCGC CA  22

MUTANT HUMAN HEDGEHOG GENE

STATEMENT AS TO FEDERALLY SPONSORED RESEARCH

This invention was made with Government support under Grant no. AR39959, awarded by the National Institutes of Health. The Government has certain rights in this invention.

INTRODUCTION

Life requires balance. At all levels, from populations, individuals, cells, and even down to biochemical signals within a cell, there is a balance of opposing forces. Replication is a particularly important process to keep under tight control, with cancer serving as an archetype for uncontrolled cell growth. Unraveling both sides of the biochemical signals that regulate growth has provided insight into the mechanisms of tumor cell transformation.

Many genes involved in the regulation of growth and control of cellular signaling are also involved in oncogenesis. Such genes may be oncogenes, which are typically upregulated in tumor cells, or tumor suppressor genes, which are down-regulated or absent in tumor cells. Malignancies can arise when a tumor suppressor is lost and/or an oncogene is inappropriately activated. Information about these regulatory signals can be used in cancer diagnosis and treatment. This knowledge can also be exploited to counteract situations where there is inadequate cell growth.

Segment polarity genes were originally discovered as mutations in flies that change the pattern of body segment structures. Mutations in these genes cause animals to develop changed patterns on the surfaces of body segments; the changes affecting the pattern along the head to tail axis. Among the genes in this class are hedgehog, which encodes a secreted protein (HH), and patched (PTC), which encodes a protein structurally similar to transporter proteins. The hedgehog gene of flies has at least three vertebrate relatives: Sonic hedgehog (SHH); Indian hedgehog (IHH), and Desert hedgehog (DHH). Based on genetic experiments in flies, patched and hedgehog have antagonistic effects in development. PTC down regulates transcription of itself, members of the transforming growth factor β and Wnt gene families, and possibly other genes. Among other activities, HH up regulates expression of patched and other genes that are negatively regulated by patched.

Recently, interest in the human hedgehog signaling pathway was piqued by the discovery of inherited patched gene mutations in patients with basal cell nevus syndrome, a rare autosomal dominant disease characterized by developmental abnormalities and frequent skin carcinomas. Somatically acquired mutations of the patched gene have been identified in sporadic cancers, including basal cell carcinomas, primary breast carcinomas, medulloblastomas and meningiomas. It is currently believed that patched acts as a tumor suppressor, and that these mutations cause a loss of function in the patched gene product. The hedgehog/patched signaling pathway may therefore be a factor in tumorigenesis.

Detecting genetic alterations that lead to increased cell growth and tumorigenesis is of great interest for clinical medicine. Identifying the specific changes that lead to altered cell growth may open the door to improved diagnosis and possible treatment for associated tumors.

Relevant Literature

Discussion of the role of hedgehog may be found in Riddle et al. (1993) *Cell* 75:1401–1416; Echelard et al. (1993) *Cell* 75:1417–1430; Krauss et al. (1993) *Cell* 75:1431–1444 (1993); Tabata and Kornberg (1994) *Cell* 76:89–102; Heemskerk and DiNardo (1994) *Cell* 76:449–460; and Roelink et a!. (1994) Cell 76:761–775.

Marigo et at. (1995) *Genomics* 28:44–51 provide gene sequences for the wild-type human hedgehog genes. Hedgehog proteins are synthesized as approximately 300 amino acid precursors. An amino terminal signal peptide is released, and the remaining protein is auto-catalytically cleaved to generate a membrane bound N-terminal portion and a soluble C-terminal portion (Porter et al. (1995) *Nature* 374:363–366). The N-terminal portion, extending from approximately amino acid 26 to amino acid 256, appears to be the active fragment involved in signaling (Feitz etal. (1995) *Current Biology* 6:643–650). It is apparently bound to the membrane by a lipophilic cholesterol moiety attached to its cleaved C-terminus (Porter et al. (1996) *Cell* 86:21–34; Porter et al. (1996) *Science* 274:255–259). The crystal structure of the N-terminus suggests the presence of a potential zinc hydrolase catalytic site (Hall et al. (1995) *Nature* 378:212–216).

Descriptions of patched gene function may be found in Hooper and Scott (1989) *Cell* 59:751–765; Nakano et al. (1989) *Nature* 341:508–513; and Goodrich et al. (1996) *Genes Develop.* 10:301–312. The association of patched mutations with basal cell nevus syndrome and sporadic tumors are described in Johnson et al. (1996) *Science* 272:1668–1671; Hahn et al. (1996) *Cell* 85:841–851; and Gailani et al. (1996) *Nature Genetics* 14:78–81.

SUMMARY OF THE INVENTION

Isolated nucleic acid compositions encoding mutated forms of human hedgehog genes are provided. The mutated form of the sonic hedgehog (SHH) protein product is associated with oncogenic transformation. The nucleic acid compositions, and antibodies specific for the mutated protein product are useful as diagnostics to identify HH-associated cancers. The nucleic acid compositions are also used to produce the encoded protein, which may be employed for functional mapping studies, as a therapeutic, and in studying associated physiological pathways. Down-regulation of the mutated gene activity in vivo is useful for therapeutic purposes.

DATABASE REFERENCES FOR NUCLEOTIDE AND AMINO ACID SEQUENCES

The complete mRNA sequence encoding human sonic hedgehog (SHH) has the Genbank accession number L38518. The gene is located on human chromosome 7q36, and has the genome database accession number GDB:456309. A partial sequence of human indian hedgehog (IHH) mRNA, 5' end, has the Genbank accession number L38517. The gene is located on human chromosome 2pter, and has the genome database accession number GDB:511203. A partial sequence of human desert hedgehog (hDHH) mRNA, has the Genbank Accession number U59748.

DESCRIPTION OF THE SPECIFIC EMBODIMENTS

Human hedgehog gene and gene product compositions are provided. The genes encode a mutant form of hedgehog that is associated with tumorigenesis. The subject genes and fragments thereof, encoded protein, and antibodies specific for the mutated protein are useful in characterizing the phenotype of associated sporadic tumors. Certain human tumors, e.g. basal cell carcinomas, breast carcinomas, medulloblastomas, etc., have been found to have an oncogenic mutation in the sonic hedgehog gene that results in an amino acid substitution at position 133 [*his133 SHH]. Tumors may be typed or staged by detection of mutated sequences, antibody detection of abnormal protein products, and functional assays for altered hedgehog activity. The encoded protein is useful in drug screening for compositions that antagonize or otherwise modulate HH activity or expression. The encoded protein is also used as a therapeutic, to modulate cell proliferation and differentiation, and treatment of pathological conditions associated with decreased hedgehog signaling.

As used herein, the term hedgehog (HH) genes and encoded proteins shall be used to generally designate any of the mammalian hedgehog genes and gene products, and unless otherwise stated will be the human homolog. Hedgehog genes may be characterized by sequence similarity to known hedgehog genes, and usually have at least about 75% sequence identity at the nucleotide, more usually at least about 85% sequence identity, and may have as much as 90% sequence identity. Methods for identifying genes by nucleic acid hybridization, or by using sequence comparison algorithms, are known in the art. Known members of the Hedgehog gene family include sonic, indian and desert hedgehog. Oncogenic mutations in HH are associated with the transformation of normal cells to tumor cells. Specific examples of oncogenic mutations are described below.

Hedgehog mutations that result in an amino acid substitution or deletion at the position corresponding to his133 in SHH, will be generally referred to as [*his HH]. This amino acid position corresponds to position 50 of the previously referenced desert hedgehog protein (DHH), and position 39 of the previously referenced indian hedgehog protein (IHH). The alignment of amino acid sequences from the three hedgehog proteins is as follows, with the histidine residue underlined, and asterisks denoting identity between two sequences.

(DHH) SEQ ID NO:1 NALAIAVMNMWPGVRLRVTEGWDEDGHHAQ
                  *** * * * ***  
(SHH) SEQ ID NO:2 NALAISVMNQWPGVKLRVTEGWDEDGHHSE
                  * *** * **********  *
(IHH) SEQ ID NO:3 NSLAISVMNQWPGVKLRVTEGWDEDGHHSE

Specific mutations may be designated according to the affected hedgehog gene product, ie. [*his SHH], [*his DHH] and [*his IHH], by the specific amino acid substitution, ie. [his→tyr HH]; [Δhis HH], etc., or both, i.e. [his→tyr SHH]. Mutations may also be specified in terms of the DNA sequence. Proteins of particular interest have a substitution of tyrosine, phenylalanine or tryptophan for [*his HH]. The substitution of other non-polar or non-charged amino acids at this position are also of interest, i.e. alanine, valine, leucine, isoleucine, proline, methionine, glycine, serine, cysteine, asparagine and glutamine.

The mutated form of sonic hedgehog, [his→tyr SHH; SEQ ID NO:4], is associated with oncogenic transformation of human cells. This is demonstrated by the presence of the mutated DNA sequence (C→T transition at nt. 548; SEQ ID NO:5) in a number of independently arising tumors. The spontaneously occurring nucleotide change encodes a tyrosine residue, but other codons can be engineered into the gene sequence, through conventional recombinant DNA technology, to provide proteins having a similar phenotype. The high degree of homology between HH proteins in this region indicates a shared structure and function, with a similar phenotypic change resulting from this amino acid change in IHH and DHH. It is believed that this mutation alters the zinc hydrolase activity of the protein.

Other mutations of interest include an amino acid substitution of the methionine found at residue 114 of SHH, herein referred to as a [*met HH] mutation, sequences shown below, with the methionine residue underlined, and asterisks denoting identity between two sequences. The known HH proteins have a high degree of sequence identity in this region. Of particular interest is a change from met→ile, e.g. [met→ile SHH]. The gene, SEQ ID NO:10, encodes this mutated protein, SEQ ID NO:9, and was found in the germline of a basal cell carcinoma patient.

(DHH) SEQ ID NO:6 RVNALAIAVMNMWPGVRLRVTEGWDED
                  *** * * * *** *
(SHH) SEQ ID NO:7 KLNALAISVMNQWPGVKLRVTEGWDED
                  * **  ********** *
(IHH) SEQ ID NO:8 RLNSLAISVMNQWPGVKLRVTEGWDED

Nucleic Acid Compositions

The human [his→tyr SHH] amino acid sequence is provided (SEQ ID NO:4), and the encoding gene, isolated from human tumors, as (SEQ ID NO:5). In order to identify the subject oncogenic HH mutations, exonic primers from the published sequence data were used to isolate SHH genomic clones. Sequence data from the genomic clones was used to generate specific primers. These primers were used to amplify genomic DNA from primary tumors, including breast carcinomas, basal cell carcinomas and medulloblastomas. The PCR products were screened for mutations using single strand conformation polymorphism (SSCP) analysis. The specific mutation found in SEQ ID NO:5 was isolated from four independent tumors.

DNA encoding a [*his HH] protein may be cDNA or genomic DNA or a fragment thereof that encompasses the altered [*his] residue. As known in the art, cDNA sequences have the arrangement of exons found in processed mRNA, forming a continuous open reading frame, while genomic sequences may have introns interrupting the open reading frame. The term "[*his HH] gene" shall be intended to mean the open reading frame encoding such specific HH polypeptides, as well as adjacent 5' and 3' non-coding nucleotide sequences involved in the regulation of expression, up to about 1 kb beyond the coding region, in either direction.

Genomic sequences of interest comprise the nucleic acids present between the initiation codon and the stop codon, including all of the introns that are normally present in a native chromosome. It may include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller; and substantially free of flanking chromosomal sequence.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The subject [*his HH] genes are isolated and obtained in substantial purity, generally as other than an intact mammalian chromosome. Usually, the DNA will be obtained substantially free of other nucleic acid sequences that do not include a hh sequence or fragment thereof, generally being at least about 50%, usually at least about 90% pure and are typically "recombinant", i.e. flanked by one or more nucleotides with which it is not normally associated on a naturally occurring chromosome.

The subject nucleic acids may be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose and then probed with a fragment of the subject DNA as a probe. Other techniques may also find use. Detection of mRNA having the subject sequence is indicative of hedgehog gene expression in the sample.

Synthesis of HH Protein

The subject nucleic acid compositions may be employed for producing [*his HH] protein, or fragments thereof that encompass a [*his] mutation. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

The peptide may be expressed in prokaryotes or eukaryotes in accordance with conventional ways, depending upon the purpose for expression. For large scale production of the protein, a unicellular organism or cells of a higher organism, e.g. eukaryotes such as vertebrates, particularly mammals, may be used as the expression host, such as *E. coli, B, subtilis, S. cerevisiae*, and the like. In many situations, it may be desirable to express the subject hedgehog gene in a mammalian host, whereby the hedgehog gene product will be glycosylated, and secreted.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended free of other proteins, as well as of cellular debris.

The polypeptide is used for the production of antibodies, where short fragments provide for antibodies specific for the particular polypeptide, and larger fragments allow for the production of antibodies over the surface of the protein. Antibodies may be raised to the normal or oncogenic forms. Of particular interest are antibodies that specifically recognize the mutated form of the protein, ie. do not bind to the normal form. Antibodies may be raised to isolated peptides corresponding to these mutations, or to the native protein, e.g. by immunization with cells expressing HH, immunization with liposomes containing HH, etc. Such antibodies are useful in therapy and diagnosis, e.g. typing and staging of human carcinomas.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Detection of HH Associated Tumors

DNA from a patient having a tumor suspected of association with aberrant HH signaling is analyzed for the presence of an oncogenic mutation in a hh gene, e.g. a [*his HH] mutation. Genetic characterization of sporadic tumors generally requires analysis of tumor cell DNA or RNA, conveniently with a biopsy sample. The nucleic acids are screened for the presence of an oncogenic mutation, as compared to a normal sequence (previously referenced). Sporadic tumors associated with altered HH signaling include basal cell carcinomas; melanomas; squamous cell carcinomas; breast carcinomas; transitional bladder cell carcinoma; meningiomas; medullomas; fibromas of the heart and ovary; carcinomas of the lung, colon, ovary, kidney and esophagus; other carcinomas of the gut; etc.

A number of methods are available for analyzing genomic DNA sequences. Where large amounts of DNA are available, the genomic DNA is used directly. Alternatively, the region of interest is cloned into a suitable vector and grown in sufficient quantity for analysis, or amplified by conventional techniques, such as the polymerase chain reaction (PCR). The use of the polymerase chain reaction is described in Saiki, et al. (1985) *Science* 239:487, and a review of current techniques may be found in Sambrook, et al *Molecular Cloning: A Laboratory Manual*, CSH Press 1989, pp.14.2–14.33.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-arboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal HH sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences. Alternatively, where an oncogenic mutation creates or destroys a recognition site for a restriction endonuclease, the fragment is digested with that endonuclease, and the product size fractionated to determine whether the fragment was digested. Fractionation is performed by gel electrophoresis, particularly on acrylamide or agarose gels.

Analysis of tumor cells for the presence of aberrant HH proteins may be performed by immunoassay. A sample is taken from a patient suspected of having a HH-associated tumor. Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Biopsy samples are of particular interest, e.g. skin lesions, organ tissue fragments, etc. Where metastasis is suspected, blood samples may be preferred. The number of cells in a sample will generally be at least about $10^3$, usually at least $10^4$, more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the presence of abnormal HH in patient cells suspected of having an oncogenic mutation. For example, detection may utilize staining of intact cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well-known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and HH in a cell lysate, supernatant or other fluid into which the tumor cells may secrete active HH protein. Measuring the concentration of HH binding in a sample or fraction thereof may be accomplished by a variety of specific assays. A conventional sandwich type assay may be used. For example, a sandwich assay may first attach HH-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates or supernatants are then added to separately assayable supports (for example, separate wells of a microtiter plate) containing antibodies. Preferably, a series of standards, containing known concentrations of normal and/or abnormal HH is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second, detecting antibody is applied. The antibody will bind the immobilized HH with sufficient specificity such that it can be distinguished from other components present. The second antibodies may be labeled to facilitate direct, or indirect quantification of binding. Examples of labels that permit direct measurement of second receptor binding include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for HH as desired, conveniently using a labeling method as described for the sandwich assay.

Down-Regulation of HH Expression

Antisense molecules specific for the oncogenic HH genes, e.g. [*his HH], [*met HH], are used to down-regulate expression in cells suspected or shown to have [*his HH] associated tumors. Administration of the antisense molecules has the effect of decreasing the oncogenic HH activity. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted HH gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the vector is introduced and expressed in the targeted tumor cells. The transcriptional initiation will be oriented such that the antisense strand is produced as an RNA molecule. The anti-sense RNA hybridizes with the endogenous sense strand mRNA, thereby blocking expression of the targeted gene. The native transcriptional initiation region, or an exogenous transcriptional initiation region may be employed. The promoter may be introduced by recombinant methods in vitro, or as the result of homologous integration of the sequence into a chromosome. Many strong promoters are known in the art, including the β-actin promoter, SV40 early and late promoters, human cytomegalovirus promoter, retroviral LTRs, methallothionein responsive element (MRE) and tetracycline-inducible promoter constructs, etc.

Transcription vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the tumor cells, usually for a period of at least about one day, more usually for a period of at least about several days to several weeks.

Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence, preferably encompassing the [*his HH] mutation. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Oligonucleotides may additionally comprise a targeting moiety that enhances uptake of the molecule by tumor cells. The targeting moiety is a specific binding molecule, e.g. an antibody or fragment thereof that recognizes molecules present on the surface of tumor cells. Bispecific antibodies, chimeric antibodies and single chain antibodies are known in the art. Suitably prepared non-human antibodies can be humanized in various ways. Linkage between the oligonucleotide and targeting moiety may use any conventional method, for example by disulfide, amide or thioether bonds, depending on the chemistry of the oligonucleotide backbone. Preferably the linkage will be cleaved inside the cell to liberate the oligonucleotide.

Oligonucleotides can be conjugated to hydrophobic residues, e.g. cholesterol, to protect from nucleases and to improve transport across cell membranes. Alternatively, conjugation to poly-L-lysine or other polyamines may also enhance delivery to the cell. A further modification that can be made is the addition of an intercalating component, such as acridine, capable of intercalating into the target mRNA and stabilizing the resultant hybrid. Antisense oligonucleotides may be transfected in combination with an enzyme(s) that will degrade antisense-mRNA complexes in the cell, e.g. RNase H. Any protein or enzyme that can preferentially degrade or sequester the antisense-mRNA duplex may be similarly useful.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

The antisense molecules and/or other inhibitory agents are administered by contact with the tumor cells under conditions that permit entry. The molecules may be provided in solution or in any other pharmacologically suitable form for administration, such as a liposome suspension. There are many delivery methods known in the art for enhancing the uptake of nucleic acids by cells. Useful delivery systems include Sendai virus-liposome delivery systems (see Rapaport and Shai (1994) *J. Biol. Chem.* 269:15124–15131), cationic liposomes, polymeric delivery gels or matrices, porous balloon catheters (as disclosed by Shi et al. (1994) *Circulation* 90:955–951; and Shi et al. (1994) *Gene Therapy* 1:408–414), retrovirus expression vectors, and the like.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing the nucleic acids are combined in an appropriate aqueous medium, conveniently a saline medium where the total solids will be in the range of about 1–10 weight percent. After intense agitation for short periods of time, from about 5–60 sec., the tube is placed in a warm water bath, from about 25°–40° C. and this cycle repeated from about 5–10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules, particularly nucleic acids of one kbp or more. In this way oligonucleotides, plasmids, large genes, chromosomal fragments, viruses or viral segments may be introduced into cells efficiently.

The therapeutic agents are administered at a dose effective to reduce expression level of [*his HH] at least about 50%, more usually at least 80%, and preferably to substantially undetectable levels.

Therapeutic Use of HH Protein

The subject recombinantly produced HH protein may be therapeutically administered in conditions characterized by inadequate HH signaling pathway activity, or where increased HH signaling is desirable. Examples of such uses are provided in the published International Patent Application WO95/18856, herein incorporated by reference. Hedgehog biological activity includes the ability to induce or otherwise modulate formation and differentiation of various tissues, including the head, limbs, lungs, central nervous system or mesodermal patterning of embryos. Proliferation is also modulated by HH in a number of tissues. Such modulation may be achieved in in vitro or in vivo situations. For example, wound healing, bone formation, the treatment of hypoproliferative or hyperproliferative skin disorders, induction of differentiation, are affected by administration of the subject proteins.

HH is able to regulate neurogenesis, such a motor neuron inducing activity, a neuronal differentiation inducing activity or a neuronal survival promoting activity. HH also regulates organogenesis and induction of stem cell or germ cell differentiation, including the ability to induce chondrocytes or an involvement in spermatogenesis. The treatment of arthritis, e.g. osteoarthritis, rheumatoid arthritis, etc. may benefit from administration of the subject proteins, and subsequent induction of chondrocytes and cartilige formation. HH is able to regulate the growth of hair by modulating the growth of cells in the hair sheath, and can be used therapeutically for this purpose.

Administration of HH induces expression of secondary signaling molecules, such as members of TGF beta family, bone morphogenetic proteins, and members of the fibroblast growth factor family.

Many neurological disorders are associated with degeneration od discrete populations of neuronal elements and may be treated with the subject HH proteins. Specific disorders include traumatic injury, injury resulting from ischemia resulting from stroke, damage resulting from inflammation and/or infection of the nervous system, Alzheimer's disease, Parkinson's disease, Huntington's chorea, amylotrophic lateral sclerosis, spinocerebellar degenerations, and chronic immunological diseases of the central nervous system, e.g. multiple sclerosis. The subject HH proteins are also useful in treating autonomic disorders of the peripheral nervous system, such as tachycardia or atrial cardiac arrythmias arising from a degenerative condition of the nerves innervating the striated muscles of the heart.

Also of interest are in vitro uses, where HH is added to specific cell cultures, e.g. neural progenitor cells, which can terminally differentiate into neurons and glia. HH sustains the reproduction of such cells in culture, in combination with appropriate culture medium, as known in the art.

The host may be treated with intact [*his HH] protein, or an active fragment thereof, particularly a cleaved fragment as generated by normal processing. Desirably, the peptides will not induce an immune response, particularly an antibody response. Xenogeneic analogs may be screened for their ability provide a therapeutic effect without raising an immune response.

Various methods for administration may be employed. The polypeptide formulation may be given orally, or may be injected intravascularly, subcutaneously, peritoneally, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously. The amide bonds, as well as the amino and carboxy termini, may be modified for greater stability on oral administration.

The subject peptides may be prepared as formulations at a pharmacologically effective dose in pharmaceutically acceptable media, for example normal saline, PBS, etc. The additives may include bactericidal agents, stabilizers, buffers, or the like. In order to enhance the half-life of the subject peptide or subject peptide conjugates, the peptides may be encapsulated, introduced into the lumen of liposomes, prepared as a colloid, or another conventional technique may be employed that provides for an extended lifetime of the peptides.

The peptides may be administered as a combination therapy with other pharmacologically active agents. The additional drugs may be administered separately or in conjunction with the peptide compositions, and may be formulated in the same formulation.

Genetically Modified Cells and Animals

The subject nucleic acids can be used to generate transgenic animals or site specific gene modifications in cell lines. Transgenic animals may be made through homologous recombination. Alternatively, a nucleic acid construct is randomly integrated into the genome. Vectors for stable integration include plasmids, retroviruses and other animal viruses, YACs, and the like. The modified cells or animals are useful in the study of hedgehog function and regulation. A detectable marker, such as lac Z may be introduced into the hedgehog locus, where upregulation of hedgehog expression will result in an easily detected change in phenotype.

DNA constructs for homologous recombination will comprise at least a portion of a [*his HH] gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. The transgenic animals may be any non-human mammal, such as laboratory animals, domestic animals, etc. The transgenic animals may be used in functional studies, drug screening, etc., e.g. to determine the effect of a candidate drug on a HH-associated tumor.

Drug Screening Assays

Drug screening identifies agents that provide a replacement for HH function in abnormal cells. The role of HH as an oncogene indicates that agents which antagonize its function will inhibit the process of oncogenesis. Conversely, agents that mimic HH function may stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, transporter function, etc.

The term "agent" as used herein describes any molecule, e.g. protein or pharmaceutical, with the capability of altering or mimicking the physiological function of hedgehog. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of cancer or developmental abnormalities attributable to a defect in hedgehog function. The compounds may also be used to enhance hedgehog function in wound healing, aging, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt.%.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular eight, temperature is in degrees centigrade; and pressure is at or near atmospheric.

EXPERIMENTAL

Identification of Mutations in Sonic hedgehog in Human Cancers

DNA was screened from a number of human primary tumors for mutations in the SONIC HEDGEHOG (SHH) gene. Primers specific for the exons (coding region sequences) were derived from the published gene sequence (previously referenced).

BAC clones were obtained by PCR screening of human BAC DNA pools from Research Genetics, Inc. (Huntsville, Ala.) (Shizuya et al. (1992) P.N.A.S. 89:8794–8797. Briefly, DNA from BAC pools was used as a template in PCR with a specific exon 2 primer pair, SEQ ID NO:11; ACCGAGGGC TGGGACGAM GATGGC and SEQ ID NO:12; GCGAGCCAGCATGCCGTACTTGCTG. Only pools comprising a BAC that contains the sequence tag defined by the primer pair will yield an amplification product. This process is continued until a single positive BAC can be identified. A positive clone, BAC270A17, was digested with restriction enzymes and ligated with vectorette linkers, as described in Riley et aL (1990) Nucl. Acids Res. 18:2887–2890.

Exon intron boundaries were determined for the three SHH exons by sequencing PCR products amplified using the universal vectorette primer and SHH CDNA primers derived from the published sequences. The exon 2-intron 3 boundary was difficult to sequence, and so a primer from the 3' end of exon 2 was used. The following primers were used to amplify genomic SHH:

exon 1; (SEQ ID NO:13) CCGCCGCGCGCACTCG
(SEQ ID NO:14) AAGGAGCGGGTGAAATCACC
exon 2; (SEQ ID NO:15) TAACGTGTCCGTCGGTGGG
(SEQ ID NO:16) TGCTTTCACCGAGCAGTGG
exon 3 (SEQ ID NO:17) CCTCCTCCCCGAGACGC
(SEQ ID NO:18) GGCCCCCTCCCGCGCC These primers were used to amplify genomic DNA from primary human tumors: 34 independent basal cell carcinomas, 14 medulloblastomas and 6 breast carcinomas. PCR was performed using 1–100 ng genomic DNA, primers and AmpliTaq™ (Perkin Elmer, CA) under the following conditions: 95° C. 1 min denaturation, 94° C. 20 sec, 58° C. 20 sec, 72° C. 30 sec for 30 cycles followed by 72° C. 2 min.

The amplification product was used in single strand conformational polymorphism (SSCP) analysis against the wild-type SHH gene, performed according to the method of Chen et al. (1995) J. Invest Dermatol. 105:629–632. No polymorphisms were found in exons 1 and 3.

SSCP abnormalities were identified in 2 of the basal cell carcinomas, 1 of the medulloblastomas and one breast carcinoma. The aberrant SSCP bands were identical in one of the basal cell carcinomas and the two other positive tumors. No aberrantly migrating bands were found on SSCP analysis of SHH exon 2 in blood cell DNA from 100 normal persons, or from the three individuals from which the tumor cells were derived, or in exons 1 and 3. Sequencing identified the same mutation in all three tumors, a C to T transition at bp 548 (SEQ ID NO:4), predicted to cause the mutation of SEQ ID NO:5.

A second basal cell carcinoma also had an abnormally migrating band on SSCP analysis of exon 2, but the same abnormal product was also present in blood cell DNA. This is a G to A substitution at bp 493 (SEQ ID NO:9), encoding the mutated protein of SEQ ID NO:10. This individual had had at least six other basal cell carcinomas, her age at onset of the studied basal cell carcinoma was approximately 40. DNA was not available from other family members, none of whom is known to have developmental abnormalities or cancers, other than small basal cell carcinomas in both of her parents on sun exposed areas after age 60. The studies carcinoma was unusually large, involving most of one cheek, the eyelids and ear, with invasion and destruction of the facial nerve. There were no phenotypic abnormalities assciated with basal cell nevus syndrome present.

SSCP analysis of the human PATCHED gene (PTC) in these four tumors identified a missense mutation in one allele of the breast carcinoma cells. Analysis of an intragenic polymorphism and direct sequencing of the mutant allele indicated a retention of both PTC alleles in this tumor SHH expression in normal human epidermal keratinocytes was not detectable by Northern blot analysis under conditions in which PTC gene expression was easily detected, irrespective of whether the cells were cultured in low or high calcium media (0.08 or 1.2 mM). However, SHH primers did amplify a product by reverse transcriptase PCR of RNA from cultured normal human epidermal keratinocytes, and sequencing confirmed the identity of the product as authentic SHH.

DNA was extracted from keratinocytes cultured at 0.07 mM calcium using the Pharmacia Quick Prep mRNA kit. First strand cDNA was synthesized with a Gene Amp kit (Perkin Elmer) using an oligo-dT primer. cDNA was amplified by three-stage nesting using the following primers: Stage 1, (SEQ ID NO:19) CCGCCGCGCGCACTCG and (SEQ ID NO:20) GGCCCCCTCCCGCGCC; Stage 2, (SEQ ID NO:22) TGCCCACCGGGCAGGGGG and (SEQ ID NO:21) GTCCTTCACCAGCTTGGTG; Stage 3, (SEQ ID NO:22) and (SEQ ID NO:23) TCAGCCTCCCATTTGGCCGCCA.

The above results indicate that a single somatic mutation is found in cancers arising from three different tissues in independent patients. This finding indicates the importance of this mutation in carcinogenesis.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid other than an intact chromosome encoding an oncogenic human hedgehog (HH) protein that comprises an amino acid substitution or deletion at the position corresponding to position 27 in any one of SEQ ID NO:1, SEQ ID NO 2 or SEQ ID NO:3;

or a fragment of at least 18 nucleotides derived therefrom and encompassing said amino acid substitution or deletion.

2. An isolated nucleic acid other than an intact chromosome encoding an oncogenic human hedgehog (HH) protein that comprises an amino acid substitution or deletion at the position corresponding to position 10 in any one of SEQ ID NO:6, SEQ ID NO:7 or SEQ ID NO:8;

or a fragment of at least 18 nucleotides derived therefrom and encompassing said amino acid substitution or deletion.

3. An isolated nucleic acid other than an intact chromosome encoding an oncogenic hedgehog (HR) protein selected from the group consisting of human [his→tyr HH] and [met→ile HH];

or a fragment of at least 18 nucleotides derived therefrom and encompassing said [his→try HH] or [met→ile HH] mutation.

4. An isolated nucleic acid according to claim 3, selected from the group consisting of SEQ ID NO:5 and SEQ ID NO:10.

5. An expression cassette comprising a transcriptional initiation region, a nucleic acid according to claim 1 under the transcriptional regulation of said transcriptional initiation region, and a transcriptional termination region.

6. A cell comprising an expression cassette according to claim 5.

7. A cell according to claim 6, wherein said cell is a mammalian cell.

8. A cell according to claim 7, wherein said mammalian cell is human.

9. A method for producing oncogenic HH protein, said method comprising:

growing a cell according to claim 6, whereby said oncogenic HH protein is expressed, and isolating said oncogenic HH protein free of other proteins.

10. An expression cassette comprising a transcriptional initiation region, a nucleic acid according to claim 2 under the transcriptional regulation of said transcriptional initiation region, and a transcriptional termination region.

11. A cell comprising an expression cassette according to claim 10.

12. A cell according to claim 11, wherein said cell is a mammalian cell.

13. A cell according to claim 12, wherein said mammalian cell is human.

14. A method for producing oncogenic HH protein, said method comprising:

growin a cell according to claim 11, whereby said oncogenic HH protein is expressed, and isolating said oncogenic HH protein free of other proteins.

15. An isolated nucleic acid according to claim 1, wherein said amino acid substitution comprises a substitution of an amino acid selected from the group consisting of tyrosine phenylalanine or tryptophan.

16. An isolated nucleic acid of at least 18 nucleotides of contiguous sequence as set forth in SEQ ID NO:5, and encompassing the [his→tyr HH] mutation.

17. An isolated nucleic acid of at least 18 nucleotides of contiguous sequence as set forth in SEQ ID NO:10, and encompassing the [met→ile HH] mutation.

* * * * *